(12) United States Patent
Heimburger et al.

(10) Patent No.: US 6,500,427 B1
(45) Date of Patent: Dec. 31, 2002

(54) ONE-COMPONENT TISSUE ADHESIVE AND A PROCESS FOR THE PRODUCTION THEREOF

(75) Inventors: Norbert Heimburger, Marburg (DE); Peter Fuhge, Lahntal (DE); Hansjörg Ronneberger, Marburg (DE)

(73) Assignee: Aventis Behring GmbH, Marburg (DE)

( * ) Notice: Subject to any disclaimer, the term of this patent is extended or adjusted under 35 U.S.C. 154(b) by 0 days.

(21) Appl. No.: 08/326,254

(22) Filed: Oct. 20, 1994

Related U.S. Application Data

(63) Continuation of application No. 07/983,613, filed on Nov. 30, 1992, which is a continuation of application No. 07/835,118, filed on Feb. 14, 1992, now abandoned, which is a continuation of application No. 07/069,199, filed on Jul. 2, 1987, now abandoned.

(30) Foreign Application Priority Data

Jul. 5, 1986 (DE) .......................................... 36 22 642

(51) Int. Cl.$^7$ ............................................. A61K 38/48
(52) U.S. Cl. ................... 424/94.64; 424/530; 424/94.1; 514/2; 514/8; 514/802; 514/822
(58) Field of Search ............................... 424/94.64, 530, 424/94.1; 514/2, 8, 56, 802, 822; 435/184; 530/381–384

(56) References Cited

U.S. PATENT DOCUMENTS

| 4,414,976 A | * | 11/1983 | Schwarz et al. | ............. | 424/530 |
| 4,427,650 A | * | 1/1984 | Stroetmann | ................. | 424/530 |
| 4,465,623 A | * | 8/1984 | Chanas et al. | .............. | 424/530 |

\* cited by examiner

Primary Examiner—Jean C. Witz
(74) Attorney, Agent, or Firm—Finnegan, Henderson, Farabow, Garrett and Dunner, L.L.P.

(57) ABSTRACT

A description is given of a one-component tissue adhesive containing, in aqueous solution, fibrinogen, F XIII, a thrombin inhibitor, prothrombin factors, calcium ions and, where appropriate, a plasmin inhibitor and of a process for the production thereof.

This adhesive can be reconstituted from a freeze-dried form with water. It can contain aLL active substances in pasteurized form and is then free of the risk of transmission of hepatitis and HTLV III.

12 Claims, No Drawings

ONE-COMPONENT TISSUE ADHESIVE AND A PROCESS FOR THE PRODUCTION THEREOF

This is a continuation of application Ser. No. 07/983,613, filed Nov. 30, 1992, which is a continuation of application Ser. No. 07/835,118, filed Feb. 14, 1992, now abandoned, which is a continuation of application Ser. No. 07/069,199, filed Jul. 2, 1987, now abandoned.

The invention relates to a tissue adhesive which contains fibrinogen, factor XIII, a thrombin inhibitor, prothrombin factors, calcium ions and, where appropriate, a plasmin inhibitor. The accelerators which are naturally present on the wound which is to be bonded result in the thrombin which is necessary for adhesion being liberated from the prothrombin in the adhesive.

The physiological processes involved in the repair of lesions in human or animal tissues result in fibrin being deposited in the region of the injury. This is initiated by thromboplastin flowing out of the injured cells and, on contact with plasma factor VII forming factor X activator which then, together with factor V and in a complex with phospholipids and calcium, converts prothrombin into thrombin. The action of thrombin in turn results, via elimination of the fibrinopeptides A and B from fibrinogen, in fibrin monomers which aggregate to form fibrin filaments which are covalently cross-linked, with the formation of isopeptide bonds by F XIIIa, a transglutaminase which is likewise activated by thrombin. An inhibitor, namely $alpha_2$-antiplasmin, is bound by factor XIII onto the fibrin filaments and protects them from degradation by plasmin.

It is evident from this process of hemostasis and wound healing that, in addition to fibrinogen as substrate, two enzymes are required: thrombin and factor XIII.

The task of thrombin in this connection is to activate both fibrinogen and factor XIII, that is to say to convert them into their reactive form. This is the fibrin monomer in the case of fibrinogen, and is the catalytically active transglutaminase (F XIIIa) in the case of factor XIII.

European Patent 0,068,047 discloses an enriched plasma fraction which is suitable as a wound closure and contains fibrinogen, a fibrinolysis inhibitor and thrombin or prothrombin in an anhydrous system. This adhesive cannot be applied dissolved in water, but can be applied only as a powder, which is a disadvantage for use. When the mixture is dissolved in water, the components react together, and a clot is produced.

For a one-component adhesive with water as solvent it is difficult to combine the active substances in such a way and in such quantitative ratios that no premature and undesired activation takes place during the production of the adhesive, the reconstitution with a solvent and the maintenance in readiness for use and, on the other hand, a sufficiently high strength is achieved relatively quickly after application to the adhesion site.

Surprisingly, conditions allowing reproducible production of a one-component adhesive, which can be manipulated in practice, in a physiological medium have been found.

The requirements for a one-component adhesive of this type to be produced and be amenable to processing are that the relative concentrations of fibrinogen, plasmin inhibitor, F XIII, prothrombin concentrate, thrombin inhibitor and calcium ions are optimized. This particularly applies to AT III as thrombin inhibitor and to calcium ions, since the calcium ions are essential for activation of the coagulation factors. High concentrations increase the rate of thrombin formation, and Low concentrations slow it down. Hence it is necessary that the concentration of calcium ions is optimal. Since, when this is the case, the formation of thrombin cannot be ruled out, it is expedient to combine with a thrombin inhibitor, preferably AT III. This is because, on the one hand, the formation of thrombin must be ruled out during the production of the adhesive and, on the other hand, the adhesive must rapidly form a stable clot when coagulation, that is to say the deposition of a fibrin film, is initiated on contact with wound surfaces. AccordingLy, the production of a thrombin-containing one-component adhesive and its use in aqueous solution is inconceivable and, moreover, it is possible to use prothrombin only under conditions which prevent activation to thrombin during production and preparation for use. These include setting up defined concentrations of thrombin inhibitor and calcium ions.

Thus the invention relates to a tissue adhesive containing in aqueous solution fibrinogen, F XIII, a thrombin inhibitor, prothrombin factors, calcium ions and, where appropriate, a plasmin inhibitor.

It was surprising that it is possible to pack, and use as tissue adhesive, fibrinogen together with prothrombin as a so-called hypercoagulable solution which, moreover, also contains calcium ions and AT III.

An adhesive of this type according to the invention can be converted into a solid form, for example freeze-dried, and reconstituted with water. It can contain all the active substances in pasteurized form, and is then free of the risk of transmission of hepatitis and HTLV III.

The mixing ratio of the active substances fibrinogen, plasmin inhibitor, F XIII, prothrombin factors, calcium ions and AT III is such that no premature activation takes place and such that, however, the mixture spontaneously coagulates, and deposits fibrin, on contact with wound surfaces.

The time in which this takes place is consistent with clinical requirements. The one-component adhesive according to the invention does not differ in its action from the two-component systems of the state of the art.

The mixture of active substances in this adhesive is such that, in the solution for use, the concentration of fibrinogen is 70–90 mg/ml and that of the prothrombin factors is between 10 and 30 U/ml based on F II. The concentration of calcium ions, some of which are protein-bound in the adhesive, is intended to be 0.5–1 mmol/l in the solution for use. Examples of thrombin inhibitors are AT III, hirudin and heparin, and AT III is preferably used in a concentration of 0.1–1 U/ml of tissue adhesive; at this concentration it prevents, at the abovementioned concentrations of prothrombin factors and calcium ions, premature fibrin formation. On the other hand, however, it is possible to favor the latter when this appears desirable on the basis of the indication. For this purpose, it is possible to dissolve the freeze-dried adhesive in a higher final concentration of calcium ions than 0.5–1 mmol/l. However, rapid use after reconstitution is then necessary.

To produce the adhesive, the active substances are initially produced in soluble form having the highest possible activity and, where appropriate, having been pasteurized. The fibrinogen concentration should be as high as possible, since the strength of adhesion increases with increasing concentration. The fibrinogen can, for example, be produced and pasteurized as described in European Patent 0,103,196, and given the desired solubility by additives of the type of compound containing urea or guanidine residues as described in European Patent 0,085,923. Factor XIII can be pasteurized as described in European Patent 0,018,561, and the prothrombin factors can be pasteurized as described in European Patent 0,056,629.

The active substances in the preferred adhesive according to the invention in principle comprise human fibrinogen in the highest possible concentration, enriched with factor XIII and the factors of the prothrombin complex (factor II, VII, IX and X), calcium ions and antithrombin III. The tissue adhesive also contains an inhibitor which inhibits plasminogen activators and/or plasmin and thus protects the resulting fibrin from degradation by plasmin. This inhibitor may be in the form of a concomitant substance of the fibrinogen selected for the bonding, but is preferably added to the adhesive in the form of aprotinin. To improve the reconstitution of the tissue adhesive after freeze-drying, it is possible for the latter to contain albumin and/or substances which contain the urea or guanidine residue and also contain, where appropriate, an amino acid with a hydrophobic side-chain or a water-soluble fatty acid and, in addition, heparin.

The fibrinogen which is suitable and preferred for preparation of the tissue adhesive is purified and already contains factor XIII. However, apart from this, also suitable is cryoprecipitate which, experience has shown, contains $alpha_2$-antiplasmin and human albumin in addition to factor XIII. It is also possible, however, to produce an adhesive of comparable action by mixing the individual components, namely: human fibrinogen, factor XIII (from plasma or placenta), plasmin inhibitors, prothrombin factors (factor II, VII, IX and X), albumin, AT III and calcium ions, a compound with a urea or guanidine residue, or an amino acid with a hydrophobic side-chain or a water-soluble fatty acid.

The mixture of the active compounds for the adhesive is advantageously in the form of a solid, preferably a lyophilizate.

The tissue adhesive preferably contains the following quantities of active compounds, which are pasteurized where appropriate, based on 1 ml of solution for use:

65–115, preferably 70–90, mg of highly purified human fibrinogen

40–80 U of factor XIII

1–50, preferably 10–30, IU of PPSB (prothrombin factors) based on F II (prothrombin)

0–10,000 KIU of aprotinin 0.01–50, preferably 0.1–1, IU of antithrombin III

0–5 USP U heparin and 0.1–5, preferably 0.5–1 mmol/l ofcalcium ions, preferably as calcium chloride.

The adhesive can contain, for example glutamate, L-isoleucine, L-arginine or human albumin as stabilizers and solubilizers.

The mixture of the solid active compounds of the tissue adhesive can be dissolved in water, or in a solvent containing calcium ions, in a short time at 20° C. When applied to the tissue which is to be united or bonded the adhesive develops within a sufficiently short time a high bonding strength without thrombin being necessary as a second component.

Accordingly, it is possible to apply the adhesive in liquid form using a single syringe, so that preparation, manipulation and use are straightforward. The adhesive is tolerated and is completely absorbed.

This one-component adhesive does not differ, either in the bonding time or in the rupture strength, from a two-component adhesive, as has been found in bonding tests in the model of puncture wounds of the rat skin and in the bonding of small intestinal anastomoses in hogs. It is even possible to increase the bonding strength by choosing an optimal calcium ion concentration of the solution which is used to dissolve the freeze-dried active compounds.

The examples which follow are intended to illustrate the invention.

EXAMPLE 1

To produce 500 ml of tissue adhesive, 580 g of pasteurized highly purified human fibrinogen which contained 2 calcium ions per mole and had been obtained as described in European Patent 0,103,196were dissolved in 580 ml of buffer, pH 7.5 (dialysis buffer), with the following composition:

0.05 mol/l NaCl 0.005 mol/l trisodium citrate 0.3 g/100 ml L-arginine monohydrochloride.

The fibrinogen solution which had been obtained in this way was dialysed twice for 16 hours and once for 8 hours, in each case against 36 l of buffer of the same composition, at +4° C. The volume of the fibrinogen solution after the dialysis was 1.53 l. The solution was then centrifuged at 8000×g for 20 min. The optical density of the solution, measured at 280 nm, was 47. This solution was diluted with the abovementioned buffer, to which the other adhesive components had been added (see below), to an optical density (280 nm) of 35 to 37, i.e. to about 20 g/l human fibrinogen.

The specific procedure for this was as follows: the dialysed and centrifuged human fibrinogen solution (1.53 l) was filtered successively through filters of pore sizes 0.65 and $0.2\mu$ at 35 to 37° C. 117.5 ml of pasteurized F XIII concentrate, containing 350 U of F XIII/ml of physiological saline solution, was filtered through a filter of $0.2\mu$ pore size into the resulting sterile fibrinogen solution.

Then 515,000 KIU (kallikrein inhibitor units) of aprotinin, 5.13 g of Na glutamate, 33.9 ml of a human albumin solution containing 20 g/100 ml, 6.78 g of isoleucine and 10,000 U of pasteurized PPSB concentrate (prothrombin factor concentrate; activity in units based on F II), 100 U of AT III (pasteurized) and 3.1 ml of 0.1 mol/l $CaCl_2$ solution were added.

The volume was then made up to 407.5 ml with dialysis buffer. This solution was filtered through a filter of $0.2\mu$ pore size into the F XIII-containing fibrinogen solution. About 2,055 ml of solution of pH 7.5 and the following composition were obtained:

| | |
|---|---|
| human fibrinogen | 2.0 g/100 ml |
| human albumin | 0.33 g/100 ml |
| arginine | 0.3 g/100 ml |
| Na glutamate | 2.5 g/l |
| isoleucine | 3.3 g/l |
| factor XIII | 20,000 U/l |
| aprotinin | 250,000 KIU/l |
| prothrombin | 5,000 U/l (calculated as F II) |
| antithrombin III | 50 U/l |
| NaCl | 0.05 mol/l |
| trisodium citrate | 0.005 mol/l |
| calcium chloride | 0.15 mmol/l. |

The sterile solution was packed in 4 mL protions and freeze-dried. A colorless, rapidly dissolving lyophilizate was obtained.

For use as tissue adhesive, one packed portion was taken up in 1 mL of solvent.

EXAMPLE 2

To produce 125 ml of tissue adhesive, 100 g of a pasteurized, highly purified human fibrinogen fraction, obtained as described in European Patent 0,103,196, were dissolved in 112 ml of dialysis buffer and dialyzed three times against 10 l each time of the same buffer as in Example 1. The volume of the concentrated fibrinogen solution after dialysis was 269 ml. It was centrifuged at 8,000×g for 20 min. The optical density of the solution at 280 nm was 69.2. The solution was diluted with a buffer whose composition corresponds to that of the dialysis buffer, and in which all the other adhesive components have been mixed, in such a way that an optical density at 280 nm of 35–37, based on fibrinogen, was reached.

The procedure for this was as follows:

127 ml of buffer were introduced into a vessel and then 8.2 ml of human albumin solution containing 20 g of human albumin per 100 ml of solution, 6 ml aprotinin amounting to 125,000 KIU and 50 ml of prothrombin concentrate containing 2,500 U of factor II and 25 U of AT III were added. 1.65 g of L-isoleucine and 1.25 g of Na glutamate were dissolved in this, and then 40 ml of F XIII concentrate containing 10,000 U of F XIII were added, the mixture was homogenized, and the pH of the solution was adjusted to pH 7.5.

Subsequently this solution was mixed and homogenized with the fibrinogen solution which is described above and 0.75 ml of a 0.1 molar $CaCl_2$ solution, and was sterilized by filtration through a filter of pore size $0.2\mu$ at 35–37° C. About 500 ml of sterile solution of the composition as in Example 1 were obtained. This solution was packed in 4 ml quantities and freeze-dried. A colorless, rapidly dissolving lyophilizate was obtained.

For use as tissue adhesive, one packed portion is taken up in 1 ml of solvent.

What is claimed is:

1. A one-component tissue adhesive in solid form comprising as active substances fibrinogen, factor XIII, a thrombin inhibitor and prothrombin factors, wherein when said adhesive is mixed with calcium ions in an aqueous solution, the ratio of said active substances is such that there is no premature coagulation of said adhesive during preparation, and such that coagulation is initiated on contact with a wound surface.

2. A one-component tissue adhesive as claimed in claim 1, which further comprises a plasmin inhibitor as an active substance.

3. A one-component tissue adhesive as claimed in claim 2, wherein said plasmin inhibitor is aprotinin or $alpha_2$-antiplasmin.

4. A one-component tissue adhesive as claimed in claim 1, wherein the active substances are pasteurized.

5. A one-component tissue adhesive as claimed in claim 1, which comprises in solution 70–90 mg/ml fibrinogen, 10–30 U/ml (based on F II) prothrombin factors, 0.5–1 mmol/l calcium ions and 0.1–1 IU/ml AT III.

6. A one-component tissue adhesive as claimed in claim 5, which further comprises 40–80 U of factor XIII.

7. A one-component tissue adhesive as claimed in claim 1, wherein said thrombin inhibitor is antithrombin III.

8. A process for the production of a one-component tissue adhesive as claimed in claim 1, comprising adding a first solution of human factor XIII, human albumin, prothrombin concentrate, and antithrombin III in a set concentration to an aqueous isotonic second solution having a pH of about 7.5 and containing at least 16 g/l human fibrinogen, about 2 g-atoms of calcium per mol of fibrinogen and about 1–6 g/l L-arginine monohydrochloride in a set concentration; and freeze-drying the combined solution; wherein said set concentrations provide the following concentrations of active substances when said freeze-dried active substances are reconstituted in a solution having about ¼ volume of the total volume of the freeze-dried active substances:
65–115 mg/ml human fibrinogen;
40–80 U/ml factor XIII;
4–40 mg/ml human albumin;
1–50 IU/ml PPSB (prothrombin factors), based on F II (prothrombin); and
0.01–50 IU/ml antithrombin III.

9. A process as claimed in claim 8, wherein said first and second solutions are pasteurized.

10. A process as claimed in claim 8, wherein said first solution is pasteurized and said second solution is sterilized by filtration.

11. A process as claimed in claim 8, wherein said first solution further comprises as active substances at least one of aprotinin, Na glutamate and isoleucine in a set concentration such that after reconstitution of the freeze dried active substances in a solvent having about one-fourth volume of the volume of the freeze dried active substances, the following concentration ranges are obtained: 1–10,000 KIU of aprotinin/ml; 0–20 g/l Na glutamate; and 0–20 g/l isoleucine.

12. A process for the production of a one-component tissue adhesive as claimed in claim 2, which comprises making an aqueous solution containing the active substances and freeze drying said active substances to form the one-component, solid form tissue adhesive.

* * * * *